United States Patent
Schaack et al.

(10) Patent No.: US 10,329,237 B2
(45) Date of Patent: Jun. 25, 2019

(54) METHOD FOR HYDROGENATING AROMATIC COMPOUNDS

(71) Applicant: BASF SE, Ludwigshafen (DE)

(72) Inventors: Bernd Bastian Schaack, Bensheim (DE); Martin Bock, Ludwigshafen (DE); Kirsten Dahmen, Bad Duerkheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/103,652

(22) PCT Filed: Dec. 10, 2014

(86) PCT No.: PCT/EP2014/077121
§ 371 (c)(1),
(2) Date: Jun. 10, 2016

(87) PCT Pub. No.: WO2015/086639
PCT Pub. Date: Jun. 18, 2015

(65) Prior Publication Data
US 2016/0304436 A1    Oct. 20, 2016

(30) Foreign Application Priority Data
Dec. 11, 2013  (EP) .................... 13196585

(51) Int. Cl.
C07C 209/72    (2006.01)

(52) U.S. Cl.
CPC ........ *C07C 209/72* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 5,773,657 A * | 6/1998 | Rutter | B01J 21/04 502/313 |
| 5,936,126 A | 8/1999 | Ruehl et al. | |
| 2009/0305869 A1 | 12/2009 | Henkelmann et al. | |
| 2011/0137083 A1 | 6/2011 | Pfeffinger | |
| 2011/0196181 A1 * | 8/2011 | Becker | C07C 5/10 585/269 |

FOREIGN PATENT DOCUMENTS

| | | |
|---|---|---|
| CN | 102503838 A | 6/2012 |
| DE | 195 33 718 A1 | 3/1997 |
| EP | 0 443 344 A2 | 8/1991 |
| EP | 0 796 839 A1 | 9/1997 |
| EP | 0 813 906 A2 | 12/1997 |
| EP | 1 106 600 A2 | 6/2001 |
| EP | 1 337 331 B1 | 1/2007 |
| EP | 1 366 812 B1 | 2/2009 |
| JP | 44-5381 | 3/1969 |
| JP | 2004-203875 A | 7/2004 |
| WO | WO 2008/015135 A2 | 2/2008 |
| WO | WO 2009/153123 A1 | 12/2009 |
| WO | WO 2010/005859 A2 | 1/2010 |
| WO | WO 2011/003899 A1 | 1/2011 |
| WO | WO 2011/033104 A1 | 3/2011 |

OTHER PUBLICATIONS

Smiley, R. Phenylene and Toluenediamines: Ullman's Encyclopedia of Industrial Chemistry, vol. 26, published online Jun. 15, 2000, pp. 617-622 URL (http://onlinelibrary.wiley.com/doi/10.1002/14356007.a19_405/pdf).*

International Search Report issued Jun. 9, 2015, in PCT/EP2014/077121 filed Dec. 10, 2014.

International Preliminary Report on Patentability issued Jun. 16, 2016 in PCT/EP2014/077121 filed Dec. 10, 2014.

Guangyin Fan et al., "Highly Efficient Hydrogenation of Methyl Propionate to Propanol over Hydrous Zirconia Supported Ruthenium", Chinese Journal of Chemistry, vol. 29, No. 2, 2011, pp. 229-236, XP055121946.

Jianqiang Wang, et al., "Partial Hydrogenation of Benzene to Cyclohexene on a Ru—Zn/m-$ZrO_2$ nanocomposite catalyst", Applied Catalysis A : General, 272, 2004, pp. 29-36.

* cited by examiner

*Primary Examiner* — Sudhakar Katakam
*Assistant Examiner* — Jennifer C Sawyer
(74) *Attorney, Agent, or Firm* — Oblon, McClelland, Maier & Neustadt, L.L.P.

(57) ABSTRACT

The present invention relates to a method for hydrogenating aromatic compounds with hydrogen in the presence of a catalyst, in which the catalyst comprises ruthenium on a zirconium oxide support material, and also the use of a catalyst comprising ruthenium on a zirconium oxide support material for hydrogenating aromatic compounds.

15 Claims, No Drawings

METHOD FOR HYDROGENATING AROMATIC COMPOUNDS

The present invention relates to a method for hydrogenating aromatic compounds with hydrogen in the presence of a catalyst, in which the catalyst comprises ruthenium on a zirconium oxide support material, and also the use of a catalyst comprising ruthenium on a zirconium oxide support material for hydrogenating aromatic compounds.

Methods for hydrogenating organic compounds, particularly for hydrogenating aromatic amines to the corresponding cyclohexane derivatives, are already known from the prior art.

WO 2009/153123 A1 discloses a continuous method and a reactor for hydrogenating organic compounds in a multiphasic system in the presence of a homogeneous or heterogeneous catalyst, in which the method is carried out in two stages. Possible catalysts disclosed by this document are heterogeneous catalysts comprising, for example, noble metals such as platinum, palladium, ruthenium and rhodium or other transition metals such as molybdenum, tungsten and chromium. These heterogeneous catalysts may be present on support materials. Support materials of this kind are, for example, carbon, aluminum oxide, silicon dioxide, zirconium dioxide, zeolites, aluminosilicates or mixtures of these support materials. In example 1, an MDA melt was hydrogenated in the presence of a suspended Ru(IV) oxide hydrate catalyst. Working examples for hydrogenating MDA in the presence of Ru, supported on zirconium oxide, are not included in the application. In this method, aromatic compounds comprising amino substituents preferably used as substrates are, for example, polymer MDA, aniline, 2,4-diaminotoluene, 2,6-diaminotoluene, o-phenylenediamine, etc. The heterogeneous catalysts are used in suspension.

DE 19553718 A1 discloses a method for hydrogenating aromatic compounds in which at least one amino group is attached to an aromatic ring. For this purpose, a heterogeneous catalyst comprising ruthenium and optionally at least one metal of the I, VII or VIII transition group may be included. The support material used is, for example, aluminum oxide, silicon dioxide, titanium dioxide or zirconium dioxide, preferably aluminum dioxide or zirconium dioxide. Only a catalyst comprising ruthenium on aluminum oxide, but not zirconium oxide, as the support material is given as an example.

EP 1337331 B1 discloses a method for the catalytic hydrogenation of aromatic or hetero-aromatic amines, wherein the active metal is ruthenium and the catalyst comprises at least one further metal from the I, VII or VIII transition group and these are applied to a support material having a BET($N_2$) surface area of less than 10 m$^2$/g. 4,4'-MDA and isomers thereof, for example, are used as aromatic compounds.

EP 1366812 B1 discloses a method for the hydrogenation of an aromatic amine which is carried out in the presence of ruthenium as active metal on a support material. The method is characterized in that the BET surface area of the support material used is in the range of greater than 30 m$^2$/g to less than 70 m$^2$/g. The support materials disclosed are, inter alia, aluminum oxide, silicon oxide, titanium oxide and zirconium oxide. Only aluminum oxide is used in the examples as support material but not zirconium oxide.

WO 2011/003899 A1 discloses a method for hydrogenating organic compounds, for example, aromatic compounds. For this purpose, a heterogeneous catalyst comprising noble metals such as platinum, palladium, ruthenium, osmium, iridium and rhodium or other transition metals can be used. The support materials mentioned are, for example, aluminum oxide, silicon dioxide, titanium dioxide and activated carbon.

WO 2011/033104 A1 discloses a composition comprising at least one epoxide resin and a mixture comprising stereoisomers of diaminomethylcyclohexane and a method for the preparation of this composition. The preparation is conducted in this case by hydrogenating the corresponding aromatic compounds in the presence of a catalyst comprising, for example, rhodium, ruthenium, palladium, platinum or nickel. The support materials used may be aluminum oxide, silicon oxide and carbon. The hydrogenation may be carried out continuously or in batch mode, both in suspension.

EP-0-796 839 A1 discloses a method for the continuous preparation of a mixture of amino-methylcyclohexanes and diaminomethylcyclohexanes by catalytic hydrogenation of amino-toluenes and diaminotoluenes with hydrogen using a fixed bed catalyst composed of an aluminum oxide support material treated with compounds of ruthenium, rare earth metals, manganese and also alkali metal hydroxides or alkaline earth metal hydroxides.

EP-0-443 344 A2 discloses a method for preparing 1-methyl-2,6-cyclohexanediamine. For this purpose, a suspension catalyst comprising rhodium on aluminum oxide is used and 2,6-toluenediamine is hydrogenated with hydrogen.

The methods known from the prior art for hydrogenating aromatic compounds to obtain the corresponding cyclohexane derivatives still have potential for improvement with respect to the tendency for deactivation of the catalysts used. In the methods from the prior art, the catalyst used suffers a deactivation after a relatively short period, i.e., the effective conversion to the desired product declines. In the methods known from the prior art, moreover, in which the catalyst is used in a fixed bed, the problem of sintering of the catalysts and/or coke formation on the catalyst frequently occurs.

Therefore, the object of the present invention is to provide an appropriate method for hydrogenating aromatic amines in which a catalyst is used having a particularly high activity over a long time period such that a high conversion at high selectivity can be achieved over a long time period. Furthermore, the method according to the invention is intended to be operated in a fixed bed or in suspension without the disadvantages known in methods from the prior art occurring, for example, coke formation or sintering of the catalyst used in a fixed bed reaction.

These objects were achieved by the method according to the invention for hydrogenating aromatic compounds with hydrogen in the presence of a catalyst, in which the catalyst comprises ruthenium on a zirconium oxide support material. The objects were further achieved by the use of a catalyst comprising ruthenium on a zirconium oxide support material for hydrogenating aromatic compounds.

The present invention is distinguished by the fact that a catalyst, comprising ruthenium on a zirconium oxide support material, is used in a fixed bed or in suspension.

In general, all aromatic compounds may be converted with hydrogen to the corresponding hydrogenation products by the method according to the invention.

Suitable aromatic compounds for the hydrogenation by the method according to the invention are:
aromatic monoamines such as aniline, isomers of toluidines, isomers of xylidines, 1- or 2-amino-naphthalene, benzidine and substituted benzidines, aromatic diamines such as isomers of phenylenediamines (o-phenylenediamine, m-phenylenediamine, p-phenylenediamine), isomers of toluylenediamines such as 2,4-diaminotoluene, 2,6-diaminotoluene, 2,3-diaminotoluene, 2,5-diaminotoluene, 3,4-diaminotoluene, 3,5-diaminotoluene, isomers of diaminonaphthalenes such as 1,5-diaminonaphthalene, meta-xylenediamine (MXDA), bis(4-amino-3-methylphenyl)-methane and bis(4-amino-3,5-dimethylphenyl)methane, aromatic mono- and dicarboxylic acids and esters thereof such as benzoic acid, isomers of phthalic acids and also esters thereof, preferably methyl esters thereof, aromatic aminocarboxylic acids and esters thereof such as anthranilic acid, aromatic alcohols such as phenol and bisphenol A, and also aromatic hydrocarbons such as benzene, toluene, ethylbenzene, isomers of xylols, indene, tetralin and naphthalene.

In a particularly preferred embodiment, the present invention relates to the method in accordance with the invention, wherein the organic compound is an aromatic amine, preferably further selected from the group consisting of aniline, 2,4-diaminotoluene (2,4-TDA), 2,6-diaminotoluene (2,6-TDA), 2,3-diaminotoluene, 2,5-diaminotoluene, 3,4-diaminotoluene, 3,5-diaminotoluene, o-phenylenediamine, m-phenylenediamine, p-phenylenediamine, m-xylenediamine (MXDA), bis(4-amino-3-methylphenyl)methane, bis(4-amino-3,5-dimethylphenyl)-methane and mixtures thereof.

Mixtures which may be used in accordance with the invention may generally comprise the abovementioned compounds and/or isomers thereof in any possible composition.

In the method according to the invention, very particular preference is given to using a mixture of the isomers of toluenediamine (TDA), preferably a mixture comprising 10 to 30% by weight, particularly preferably 15 to 25% by weight, for example 20% by weight of 2,6-TDA and 70 to 90% by weight, particularly preferably 75 to 85% by weight, for example 80% by weight of 2,4-TDA, in which the sum of the amounts of both 2,6-TDA and 2,4-TDA add up to 100% by weight. In this particularly preferred embodiment of the method according to the invention, a mixture of the isomers of methyldiaminocyclohexane (MDACH) is obtained as product.

The present invention therefore preferably relates to the method according to the invention in which the organic compound is a mixture of 2,4- and 2,6-diaminotoluene, in which the 2,4-diaminotoluene is present in a proportion of 70 to 90% and the 2,6-diaminotoluene in a proportion of 10 to 30%.

The method according to the invention can generally be carried out continuously or in batch mode. In a preferred embodiment, the present invention relates to the method in accordance with the invention in which said method is carried out continuously.

In the batchwise reaction procedure, the hydrogenation may be carried out, for example, in a stirred tank or stirred autoclave, a loop reactor, a jet loop reactor, a bubble column or a fixed bed reactor with pumping circuit. The batchwise hydrogenation is preferably carried out in a stirred tank or stirred autoclave.

In the continuous reaction procedure, the hydrogenation is typically carried out in a continuously operating stirred tank reactor, a continuously operating loop reactor, a continuously operating jet loop reactor, a continuously operating bubble column or a continuously operating fixed bed reactor with pumping circuit or a stirred tank cascade. The batchwise hydrogenation is preferably carried out in a stirred tank or stirred autoclave.

The method is preferably carried out in trickle reactors or in flooded mode by the fixed bed method, according to WO 2008/015135 A1, for example. The hydrogen may be passed over the catalyst either in cocurrent with the solution of the reactant to be hydrogenated or in countercurrent.

Suitable apparatus for performing a hydrogenation over a fluidized catalyst bed and over a fixed catalyst bed are known from the prior art, for example from Ullmanns Enzyklopädie der Technischen Chemie, 4th edition, Vol. 13, pp. 135 ff., and also from P. N. Rylander, "Hydrogenation and Dehydrogenation" in Ullmann's Encyclopedia of Industrial Chemistry, 5th ed. on CD-ROM.

Suitable reactors for performing the method according to the invention in suspension mode are known per se to those skilled in the art, for example, stirred tank or bubble column. It is also possible to operate the method according to the invention in a cascade of multiple suspension reactors connected in series, for example, in a stirred tank cascade or a bubble column cascade, for example, with at least three appropriate reactors connected in series in each case.

In order to achieve a complete conversion, a postreaction of the hydrogenation residue may be conducted. For this purpose, the hydrogenation residue may subsequently be passed through the hydrogenation process in the gas phase or in the liquid phase in a direct pass or pumped in circulation by one or more reactors connected in series. In liquid phase hydrogenation, the reactor may be operated in trickle mode or flooded mode. The reactor is charged with the catalyst according to the invention or with another catalyst known to those skilled in the art.

The method according to the invention is generally carried out at a pressure of 50 to 500 bar, preferably at a pressure of 100 to 300 bar. Since the method according to the invention is particularly preferably carried out without addition of a further gas besides hydrogen, the method pressure is preferably determined by the partial pressure of hydrogen. The present invention therefore particularly preferably relates to the method according to the invention, in which said method is carried out at a hydrogen pressure of 50 to 500 bar, preferably 100 to 300 bar.

The method according to the invention is carried out at a temperature of 30 to 280° C., preferably 50 to 220° C., particularly preferably 70 to 190° C.

The present invention therefore preferably relates to the method according to the invention, in which said method is carried out at a temperature of 30 to 280° C., preferably 50 to 220° C., particularly preferably 70 to 190° C.

In the method according to the invention, hydrogen is used as hydrogenating agent.

In a preferred embodiment, the hydrogen used as hydrogenating agent is used in excess based on the compound to be hydrogenated. For example, hydrogen is used as hydrogenating agent in a 1.01 to 10 fold, preferably 1.05 to 10 fold, more preferably 1 to 10 fold, particularly preferably 1.01 to 5 fold, for example 1.1 to 5 fold, stoichiometric excess. In one embodiment, the hydrogen used can be fed back as cycle gas into the reaction.

In a preferred embodiment of the method according to the invention, technically pure hydrogen is used. In the context of the present invention, "technically pure" is understood to mean a hydrogen content of at least 99.0% by weight, preferably at least 99.5% by weight.

In a further embodiment according to the invention, the hydrogen may also be used in the form of a gas comprising hydrogen. Possible in this context are, for example, mixtures comprising gases and inert gases such as nitrogen, helium, neon, argon and/or carbon dioxide. Reformer offgases, refinery gases etc, for example, may be used as gases comprising hydrogen. These hydrogen-comprising gases have a hydrogen content of, for example, 10 to 100% by weight, preferably 50 to 100% by weight.

The method according to the invention may generally be carried out in the presence or absence of at least one solvent. The method is particularly preferably carried out in an organic solvent. In a further preferred embodiment, the method according to the invention is carried out in bulk, i.e. as a melt in the absence of a solvent.

The use of solvents is advantageous, for example, when the organic compound is a solid and cannot, or only with great difficulty, be handled and conveyed as a melt. Suitable solvents are, for example, selected from the group consisting of alcohols such as isopropanol, isobutanol or t-butanol, ethers such as diethyl ether, glycol dimethyl ether (diglyme), glycol dipropyl ether (proglyme), dioxane or tetrahydrofuran, and mixtures thereof. In a further embodiment according to the invention, the end product methyldiaminocyclohexane formed in the reaction or the low boilers formed, methylcyclohexylamine for example, are used as solvent.

If the method according to the invention is carried out in the presence of a solvent, this is generally used in such an amount so that a 10 to 50% by weight, preferably 15 to 40% by weight, particularly preferably 20 to 30% by weight, solution of the organic compounds designated to be hydrogenated is present.

Ruthenium on a zirconium oxide support material is used as catalyst according to the invention.

Catalysts of this kind can be prepared by known methods such as impregnation or saturation, as described for example in A. B. Stiles, Catalyst Manufacture-Laboratory and Commercial Preparations, Marcel Dekker, New York, 1983, or precipitation or deposition, as described for example in EP 1 106 600, page 4, and A. B. Stiles, Catalyst Manufacture, Marcel Dekker Inc., 1983, page 15.

The preparation of the catalysts to be used in accordance with the invention can be undertaken such that suitable ruthenium compounds, for example, ruthenium salts are applied to the zirconium oxide support material in the form of extrudates, pills or spheres having diameters, for example, of about 1.5 to 10 mm. The latter is then dried, generally at a temperature of 80 to 180° C., for example 120° C., and calcined at a temperature of 180 to 450° C., for example 180° C.; both steps can also be carried out simultaneously. Suitable ruthenium salts for the application are selected, for example, from the group consisting of ruthenium acetate, acetylacetonate, chloride, nitrosylnitrate and mixtures thereof.

An appropriately prepared catalyst is basically available for use according to the invention after drying. In a preferred manner, however, particularly preferably after arrangement in the reactor intended for the hydrogenation according to the invention but before use, said catalyst is activated by treatment with hydrogen at a temperature of, for example, 150 to 400° C. Ruthenium is present on the catalyst used according to the invention, preferably in a total amount of 0.05 to 15% by weight or more than 15 to 20% by weight, i.e. 0.05 to 20% by weight, preferably 0.05 to 12% by weight or more than 12 to 15% by weight, i.e. 0.05 to 0.05 to 20% by weight, particularly preferably 0.1 to 11% by weight or more than 11 to 14% by weight, i.e. 0.1 to 14% by weight, based on the total weight of the catalyst in each case.

The zirconium oxide ($ZrO_2$) support material is preferably present in accordance with the invention in monoclinic, tetragonal, cubic or amorphous phase or a mixed phase of these modifications, particularly preferably in monoclinic, tetragonal or a mixed phase of these modifications.

The present invention thus preferably relates to the method according to the invention in which the zirconium oxide support material is present in monoclinic, tetragonal, cubic or amorphous phase or a mixed phase of these modifications, particularly preferably in monoclinic, tetragonal or a mixed phase of these modifications.

The zirconium oxide support material according to the invention, preferably before applying the ruthenium, preferably has a BET surface area of 30 to 300 $m^2/g$, preferably 35 to 250 $m^2/g$, particularly preferably 50 to 90 $m^2/g$ or more than 90 to 100 $m^2/g$, i.e. 50 to 100 $m^2/g$, determined in each case by nitrogen sorption according to DIN 66131.

The catalyst used according to the invention preferably has, in accordance with the invention, a BET surface area of 30 to 300 $m^2/g$, preferably 50 to 90 $m^2/g$ or more than 90 to 100 $m^2/g$, i.e. 50 to 100 $m^2/g$, a pore volume of 0.1 to 1 $cm^3/g$, preferably 0.1 to 0.9 $cm^3/g$, and a tapped density of 500 to 2000 $kg/m^3$, preferably 700 to 1750 $kg/m^3$.

The zirconium oxide support material according to the invention, preferably before applying the ruthenium, preferably has a pore volume of 0.1 to 1 $cm^3/g$, preferably 0.1 to 0.9 $cm^3/g$, determined in each case by mercury porosimetry according to DIN 66133.

If the method according to the invention is carried out in a fixed bed then the zirconium oxide support material, preferably before applying the ruthenium, has a pore volume of 0.1 to 1 $cm^3/g$, preferably 0.1 to 0.6 $cm^3/g$, particularly preferably 0.1 to 0.5 $cm^3/g$, determined in each case by mercury porosimetry according to DIN 66133.

If the method according to the invention is carried out in suspension then the zirconium oxide support material, preferably before applying the ruthenium, has a pore volume of 0.1 to 1 $cm^3/g$, preferably 0.5 to 1.0 $cm^3/g$, particularly preferably 0.7 to 0.9 $cm^3/g$, determined in each case by mercury porosimetry according to DIN 66133.

The zirconium oxide support material according to the invention, preferably before applying the ruthenium, preferably has a tapped density of 500 to 2000 $kg/m^3$, preferably 600 to 1800 $kg/m^3$, particularly preferably 700 to 1750 $kg/m^3$, determined in each case in a STAV2003 tap volumeter from JEL, tapping 2000 times.

The zirconium oxide support material according to the invention preferably has a BET surface area of 30 to 300 $m^2/g$, preferably 50 to 90 $m^2/g$ or more than 90 to 100 $m^2/g$, i.e. 50 to 100 $m^2/g$, determined in each case by nitrogen sorption according to DIN 66131, a pore volume of 0.1 to 1 $cm^3/g$, preferably 0.1 to 0.9 $cm^3/g$, determined in each case by mercury porosimetry according to DIN 66133, and a tapped density of 500 to 2000 $kg/m^3$, preferably 700 to 1750 $kg/m^3$, determined in each case in a STAV2003 tap volumeter from JEL, tapping 2000 times.

The zirconium oxide support material according to the invention particularly preferably has a monoclinic or tetragonal modification (or a mixture of the two), a BET surface area of 30 to 300 $m^2/g$, preferably 50 to 90 $m^2/g$ or more than 90 to 100 $m^2/g$, i.e. 50 to 100 $m^2/g$, determined in each case by nitrogen sorption according to DIN 66131, a pore volume of 0.1 to 1 $cm^3/g$, preferably 0.1 to 0.9 $cm^3/g$, determined in each case by mercury porosimetry according to DIN 66133, and a tapped density of 500 to 2000 $kg/m^3$, preferably 700 to 1750 $kg/m^3$, determined in each case in a STAV2003 tap volumeter from JEL, tapping 2000 times.

The zirconium oxide support material of the catalyst used in the fixed bed has a pore size distribution in which more than 50% of the pores present are formed by mesopores having a diameter of 2 nm to 50 nm and the remainder up to 100% by macropores having a diameter>50 nm.

The present invention therefore preferably relates to the method according to the invention, wherein the zirconium oxide support material of the catalyst used in the fixed bed has a pore size distribution in which more than 50% of the pores present are formed by mesopores having a diameter of 2 nm to 50 nm and the remainder up to 100% by macropores having a diameter>50 nm.

The zirconium oxide support material of the catalyst used in suspension has a pore size distribution in which more than 40% of the pores present are formed by macropores having a diameter of >50 nm and the remainder up to 100% by mesopores having a diameter of 2 nm to 50 nm.

The present invention therefore preferably relates to the method according to the invention, wherein the zirconium oxide support material of the catalyst used in suspension has a pore size distribution in which more than 40% of the pores present are formed by macropores having a diameter of >50 nm and the remainder up to 100% by mesopores having a diameter of 2 nm to 50 nm.

In the method according to the invention, a catalyst hourly space velocity is generally established of 0.01 to 2 kg, preferably 0.05 to 1 kg, particularly preferably 0.10 to 0.6 kg of aromatic compound to be hydrogenated per liter of catalyst per hour. Any small change in the proportion of desired product obtained, which may occur during the method according to the invention by a potentially changing activity of the catalyst in the course of particularly long reaction periods, may be compensated for by a small adjustment to the reaction temperature or other parameters. The potentially changing proportions of desired product may be monitored by analysis of the reaction mixture. This analysis can be carried out by methods known to those skilled in the art, for example, by gas chromatography (GC).

The hydrogenation mixture obtained according to the invention may be purified by the method according to the invention, for example, by distillation. Catalyst present in the reaction output may optionally be removed before the distillation, for example, by a solid-liquid separation such as filtration, sedimentation or centrifugation. Solvent and unreacted starting materials can be fed back into the process.

After successful workup, by distillation for example, the desired products according to the invention are obtained with a purity of at least 99% by weight. At this purity, the compounds mentioned can generally be used for all further processes.

The present invention also relates to the use of a catalyst comprising ruthenium on a zirconium oxide support material for hydrogenating aromatic compounds. That which has been stated with respect to the method according to the invention applies accordingly with respect to the individual features and the preferred embodiments of this usage according to the invention.

The method according to the invention and the advantages thereof are illustrated in more detail by the following examples.

EXAMPLES

Example 1

Various catalytically active metals on $Al_2O_3$ as support were tested in the method according to the invention in the hydrogenation of toluenediamine (TDA) to methyldiaminocyclohexane (MDACH) and the conversion and selectivity were measured. The reaction conditions according to the invention were:

Starting material: TDA (isomeric mixture of 2,4- and 2,6-TDA in a weight ratio of 80:20) dissolved in dioxane (25% by weight solution), temperature=170° C., hydrogen pressure=140 bar, amount of catalyst=20 mg per ml starting material. The reactions were carried out in an autoclave.

The conversion and the selectivity were determined by GC analysis (GC column: RTX® Amine, length=30 m, internal diameter=0.25 mm, film thickness=0.5 μm) and stated as area %. Table 1 shows the results obtained after a reaction time of 180 minutes.

TABLE 1

| Metal content [% by wt.] | Metal | TDA conversion [Area %] | MDACH Selectivity [Area %] |
| --- | --- | --- | --- |
| 14.8 | Mo | 3.51 | 53.01 |
| 7.0 | Co | 2.66 | 41.59 |
| 10.3 | Ni | 3.78 | 47.32 |
| 9.9 | Pd | 82.48 | 1.66 |
| 5.0 | Pt | 9.00 | 57.80 |
| 5.0 | Rh | 99.21 | 33.45 |
| 12.1 | Ru | 93.56 | 85.87 |
| 5.0 | Ir | 16.36 | 13.09 |

Ruthenium as catalytically active metal showed the highest selectivity at 85.87% at high conversion (93.56%).

The catalyst preparation is described by way of example based on the co-catalyst. All other catalysts are prepared analogously with the corresponding metal salt solution.

A bowl is charged with 10 g of aluminum oxide (NorPro no. 2009850151). 5.49 g of cobalt(II) nitrate hexahydrate is then weighed into a measuring cylinder and is diluted with 7.6 ml of distilled water. The solution is divided into four and the support material is soaked in the bowl in four steps. Between the impregnating steps, the material is homogenized with a spatula. The powder is dried for 16 h at 120° C. and subsequently calcined for 4 h at 400° C. The catalyst obtained is then reduced at 400° C. with 4 l/h $H_2$ and 40 l $N_2$/h for 2 h and subsequently passivated with 5% air and 95% $N_2$ for 2 h at room temperature.

Example 2

The catalytically active metal ruthenium was tested on various support materials by hydrogenating toluenediamine (TDA) to methyldiaminocyclohexane (MDACH) and the conversion and selectivity were measured.

The preparation of the catalyst used is described below by way of example for an inventive Ru catalyst on zirconium oxide as support material. The other catalysts mentioned in Table 2 were prepared accordingly:

A measuring cylinder is charged with 30.51 g of Ru(III) nitrosyl nitrate solution (from Heraeus) and filled to a total volume of 37.5 ml with demineralized water. A ceramic bowl is then charged with 50 g of zirconium oxide powder (D9-89, BASF, BET surface area: 78 $m^2$/g, pore volume: 0.84 ml/g, pore volume distribution: 68% macropores, 32% mesopores), the solution is added and homogeneously mixed. The powder is then dried in a circulating-air drying cabinet at 120° C. for 16 h and calcined at 200° C. for 2 h in air. The powder is then first purged with 40 l/h $N_2$ for 20 min in a rotary tube furnace and then reduced over a period of 90 min (3 l/h hydrogen and 53 l/h nitrogen). After cooling to room temperature, the hydrogen is shut off and the powder is purged with ca. 60 l/h nitrogen. For passivation purposes, firstly 60 l/h nitrogen and 1 l/h air are added and the amount of air then slowly increases to 10 l/h (0 l/h nitrogen). It must be ensured here that the catalyst is not heated above 35° C. The active composition thus prepared is 10% by weight Ru and 90% by weight $ZrO_2$.

The catalyst has the following characteristics: tapped density is 1.13 kg/L, the pore volume (Hg porosimetry) is 0.32 ml/g, the BET surface area is 75 m²/g, the pore distribution is as follows: 0% mesopores (2-50 nm), 100% macropores (>50 nm).

The reaction conditions for the hydrogenation experiments were: starting material: TDA (isomeric mixture of 2,4- and 2,6-TDA in a weight ratio of 80:20) dissolved in dioxane (25% by weight solution), temperature=170° C., hydrogen pressure=140 bar, amount of catalyst=20 mg per ml of starting material. The reactions were carried out in an autoclave.

The conversion and the selectivity were determined by GC analysis (GC column: RTX® Amine, length=30 m, internal diameter=0.25 mm, film thickness=0.5 μm) and stated as area %. Table 2 shows the results obtained after a reaction time of 180 minutes.

TABLE 2

| Support material | Ru content [% by wt.] | TDA conversion [Area %] | MDACH Selectivity [Area %] |
|---|---|---|---|
| α-Al₂O₃ | 10.0 | 15.93 | 75.88 |
| γ-Al₂O₃ | 10.2 | 80.37 | 83.75 |
| γ-, θ-, δ-Al₂O₃ | 12.1 | 82.98 | 82.16 |
| Boehmite | 11.6 | 78.40 | 77.34 |
| pseudo-Boehmite | 10.4 | 57.78 | 78.25 |
| Activated carbon | 10.0 | 59.66 | 35.11 |
| Graphite | 10.0 | 66.19 | 45.95 |
| La₂O₃ | 9.7 | 59.68 | 56.23 |
| SiO₂ | 10.0 | 45.11 | 65.99 |
| TiO₂ | 10.0 | 16.80 | 67.42 |
| Faujasite | 10.0 | 3.26 | 58.06 |
| Cr₂O₃ | 8.9 | 62.02 | 57.49 |
| HA (Hydroxyapatite) | 11.6 | 23.05 | 72.50 |
| ZrO₂ (mixture of monoclinic, tetragonal) | 10.0 | 40.06 | 85.87 |

The catalyst according to the invention comprising ruthenium on zirconium oxide as support material showed an excellent selectivity with respect to the desired product.

Various $ZrO_2$ support materials were then tested and the results are shown in Table 3. The reactions were carried out according to Example 2.

TABLE 3

| Support designation | Pore volume [mL/g] | BET surface area [m²/g] | Pore distribution (Mesopores:Macropores) | Ru content | TDA conversion | MDACH selectivity |
|---|---|---|---|---|---|---|
| D9-89 | 0.32 | 75 | 0:100 | 10 | 40 | 86 |
| NorPro XZ16122 | 0.53 | 83 | 30:70 | 9.6 | 44 | 87 |
| D9-89 (1000° C.) | 0.48 | 17 | 2:98 | 9.4 | 74 | 79 |
| NorPro SZ31164 | 0.54 | 92 | 36:64 | 9.7 | 47 | 86 |

The examples show that a low BET surface area leads to a decline in MACH selectivity and that a high BET surface area is advantageous.

The hydrogenations according to examples 3 and 4 described below were carried out in a tubular reactor (internal diameter 12 mm, length 140 cm). The reactor was operated in this case in circulating mode, i.e. the output was partially recycled to the reactor such that a superficial velocity of 30 to 60 m/h was present in the reactor.

The hydrogenation was carried out using pure hydrogen. The feed was selected such that the catalyst hourly space velocity in the reactor (kg(TDA solution)/(L(catalyst)·h) reaches the specified value. The hydrogen was supplied in a pressure-regulated manner at the specified pressure. The reaction temperatures are likewise specified.

Example 3

Comparative

In this comparative example, the deactivation tendency of a catalyst comprising 1% by weight of ruthenium on a gamma-aluminum oxide support material was tested in the hydrogenation of toluenediamine (TDA) to methyldiaminocyclohexane (MDACH) and the conversion and the selectivity were measured. The reaction conditions were:

Starting material: TDA (isomeric mixture of 2,4- and 2,6-TDA in a weight ratio of 80:20) dissolved in dioxane (25% by weight solution), temperature=170° C., hydrogen pressure=190 bar, catalyst hourly space velocity=0.5 $kg_{starting\ material} \cdot L_{catalyst}^{-1} \cdot h^{-1}$, superficial velocity 44 m/h.

The conversion and the selectivity were determined by GC analysis (GC column: RTX® Amine, length=30 m, internal diameter=0.25 mm, film thickness=0.5 μm) and stated as area %. Table 4 shows the results obtained as a function of the reaction time.

TABLE 4

| Time [h] | TDA conversion [Area %] | MDACH Selectivity [Area %] |
|---|---|---|
| 22 | 91.5 | 79.9 |
| 41 | 88.4 | 80.8 |
| 65 | 85.8 | 79.9 |
| 185 | 79.3 | 78.8 |
| 209 | 76.8 | 79.0 |
| 233 | 74.9 | 79.2 |
| 256 | 75.4 | 77.9 |
| 280 | 74.1 | 77.2 |

Comparative example 3 shows that the TDA conversion after 280 hours had fallen from 91.5% (after 22 hours) to 74.1% (after 280 hours). At the same time, the MDACH selectivity declined from 79.9% to 77.2%.

Example 4

Preparation of 1% by Weight Ru on $ZrO_2$ Fixed Bed Catalyst 238 g of $ZrO_2$ extrudates (Ø3 mm, SZ 31108 from NorPro, BET surface area: 73 m²/g, pore volume: 0.30 ml/g, pore volume distribution: 6% macropores, 94% mesopores)

are sprayed in an impregnating drum with 19.81 g of Ru(III) nitrosyl nitrate solution (15.95% by weight Ru(III) nitrosyl nitrate (from Heraeus) in dilute nitric acid), diluted with 35 ml of demineralized water.

The extrudates are then dried at 120° C. for 16 h in a circulating-air drying cabinet and subsequently calcined in a muffle furnace at 180° C. for 2 h. The catalyst is then firstly reduced for 2 h at 200° C. (4 l/h $H_2$; 40 l/h $N_2$) and passivated with a mixture of 10% by volume of air and 90% by volume of $N_2$ for 1 h at room temperature. The active composition thus prepared comprises 1% by weight Ru and 99% by weight zirconium oxide.

The catalyst has the following characteristics: a BET surface area of 81 $m^2$/g, a tapped density of 1.2 kg/L, a pore volume of 0.24 mL/g (determined by Hg porosimetry).

Example 5

In this example according to the invention, the reaction was carried out according to comparative example 3, in which the inventive catalyst comprising 1% by weight ruthenium on a zirconium oxide support material was used, the preparation of which is shown in example 2 by way of example. The reaction conditions were:

Starting material: TDA (isomeric mixture of 2,4- and 2,6-TDA in a weight ratio of 80:20) dissolved in dioxane (25% by weight solution), temperature=170° C., hydrogen pressure=190 bar, catalyst hourly space velocity=0.1 $kg_{starting\ material} \cdot L_{catalyst}^{-1} \cdot h^{-1}$, superficial velocity 44 m/h.

The conversion and the selectivity were determined by GC analysis (GC column: RTX® Amine, length=30 m, internal diameter=0.25 mm, film thickness=0.5 μm) and stated as area %. Table 5 shows the results obtained as a function of the reaction time.

TABLE 5

| Time [h] | TDA conversion [Area %] | MDACH Selectivity [Area %] |
|---|---|---|
| 18.0 | 97.9 | 53.2 |
| 26.0 | 97.6 | 61.0 |
| 42.0 | 96.6 | 73.3 |
| 73.0 | 96.8 | 69.2 |
| 146.0 | 95.5 | 76.1 |
| 170.0 | 95.3 | 76.0 |
| 193.5 | 94.9 | 76.3 |
| 218.5 | 94.6 | 76.7 |
| 242.0 | 94.1 | 76.1 |
| 330.0 | 88.2 | 74.5 |
| 354.0 | 89.5 | 71.8 |
| 380.5 | 94.4 | 75.4 |
| 402.0 | 94.8 | 75.4 |
| 475.0 | 95.6 | 75.4 |
| 498.0 | 94.9 | 78.0 |
| 522.5 | 95.4 | 75.8 |
| 572.5 | 95.6 | 75.5 |
| 650.0 | 95.0 | 76.5 |
| 672.0 | 95.5 | 75.8 |
| 696.5 | 95.6 | 75.5 |
| 720.0 | 95.5 | 75.5 |
| 744.0 | 95.4 | 76.1 |
| 818.0 | 94.8 | 78.1 |
| 840.0 | 95.2 | 75.8 |
| 864.0 | 95.2 | 75.8 |
| 890.0 | 95.2 | 75.9 |

The example shows that the TDA conversion after 242 hours is 94.1% and after 890 hours is 95.2%, in which the MDACH selectivity at 242 hours and 890 hours is high and practically unchanged.

Example 6

In this inventive example, the reaction was carried out according to comparative example 3, wherein the catalyst according to the invention comprising 1% by weight ruthenium on a zirconium oxide support material was used, the preparation of which is shown in Example 2 by way of example. The reaction conditions were:

Starting material: TDA (isomeric mixture of 2,4- and 2,6-TDA in a weight ratio of 80:20) dissolved in methyldiaminocyclohexane (15% by weight solution), temperature=185° C., hydrogen pressure=190 bar, catalyst hourly space velocity=0.5 $kg_{starting\ material} \cdot L_{catalyst}^{-1} \cdot h^{-1}$, superficial velocity 44 m/h.

The conversion and the selectivity were determined by GC analysis (GC column: RTX® Amine, length=30 m, internal diameter=0.25 mm, film thickness=0.5 μm) and stated as area %. Table 6 shows the results obtained as a function of the reaction time.

TABLE 6

| Time [h] | TDA conversion [Area %] | MDACH selectivity [Area %] |
|---|---|---|
| 89 | 77 | 70 |
| 281 | 79 | 87 |
| 617 | 77 | 88 |
| 840 | 83 | 87 |

The example shows that the hydrogenation is also possible in substance and does not lead to a decrease in the conversion and the selectivity over a period of at least 840 hours.

Example 7

In this inventive example, the reaction was carried out according to comparative example 3, wherein the catalyst according to the invention comprising 2% by weight ruthenium on a zirconium oxide support material was used, the preparation of which was carried out analogously to Example 2 with correspondingly higher amount of Ru. The reaction conditions were:

Starting material: TDA (isomeric mixture of 2,4- and 2,6-TDA in a weight ratio of 80:20) dissolved in methyldiaminocyclohexane (15% by weight solution), temperature=150° C., hydrogen pressure=190 bar, catalyst hourly space velocity=0.5 $kg_{starting\ material} \cdot L_{catalyst}^{-1} \cdot h^{-1}$, superficial velocity 44 m/h.

The conversion and the selectivity were determined by GC analysis (GC column: RTX® Amine, length=30 m, internal diameter=0.25 mm, film thickness=0.5 μm) and stated as area %. Table 7 shows the results obtained as a function of the reaction time.

TABLE 7

| Time [h] | TDA conversion [Area %] | MDACH selectivity [Area %] |
|---|---|---|
| 256 | 76 | 89 |
| 599 | 82 | 88 |
| 2993 | 80 | 85 |

The example shows that the hydrogenation is also possible in substance and does not lead to a decrease in the conversion and the selectivity over a period of at least 2993 hours.

Example 8

In this inventive example, the reaction was carried out according to comparative example 3, wherein the catalyst according to the invention comprising 5% by weight ruthenium on a zirconium oxide support material was used, the preparation of which was carried out analogously to Example 2 with correspondingly higher amount of Ru. The reaction conditions were:

Starting material: TDA (isomeric mixture of 2,4- and 2,6-TDA in a weight ratio of 80:20) dissolved in methyl-diaminocyclohexane (15% by weight solution), temperature=185° C., hydrogen pressure=190 bar, catalyst hourly space velocity=0.5 $kg_{starting\ material} \cdot L_{catalyst}^{-1} \cdot h^{-1}$ superficial velocity 44 m/h.

The conversion and the selectivity were determined by GC analysis (GC column: RTX® Amine, length=30 m, internal diameter=0.25 mm, film thickness=0.5 µm) and stated as area %. Table 8 shows the results obtained as a function of the reaction time.

TABLE 8

| Time [h] | TDA conversion [Area %] | MDACH selectivity [Area %] |
|---|---|---|
| 200 | 64 | 96 |
| 250 | 64 | 96 |

The example shows that the hydrogenation is also possible in substance and does not lead to a decrease in the conversion and the selectivity over a period of at least 250 hours.

Example 9

The continuous hydrogenation of TDA in a suspension autoclave was carried out in a 270 ml autoclave with baffles and a stirrer with 6-blade impeller. This was initially charged with 6 g of pulverulent 5% Ru/ZrO$_2$ catalyst, prepared according to Example 4, in a mixture comprising MDACH and dioxane in a ratio of 25:75 percent by weight and hydrogen was continuously metered in at 15 NL/h. At 170° C. and 180 bar, 12 g of a solution comprising 25% by weight TDA and 75% by weight dioxane were then fed in per hour. The suspension catalyst was retained by a filter element made of sintered metal and the reaction mixture was passed continuously over the frit.

The conversion and the selectivity were determined by GC analysis (GC column: RTX® Amine, length=30 m, internal diameter=0.25 mm, film thickness=0.5 µm) and stated as area %. Table 9 shows the results obtained as a function of the reaction time.

TABLE 9

| Time [h] | TDA conversion [Area %] | MDACH selectivity [Area %] |
|---|---|---|
| 175 | 99.89 | 85.29 |
| 220 | 99.85 | 84.53 |
| 295 | 99.80 | 83.78 |

The example shows that the hydrogenation of TDA in a continuous suspension hydrogenation is possible without significant decline in the conversion and selectivity.

Example 10

The continuous hydrogenation of TDA in a suspension autoclave was carried out in a 270 ml autoclave with baffles and a stirrer with 6-blade impeller. This was initially charged with 6 g of pulverulent 1% by weight Ru/ZrO$_2$ catalyst, prepared according to Example 4, in a mixture comprising MDACH and dioxane in a ratio of 25:75 percent by weight and hydrogen was continuously metered in at 15 NL/h. At 170° C. and 180 bar, 12 g of a solution comprising 25% by weight TDA and 75% by weight dioxane were then fed in per hour. The suspension catalyst was retained by a filter element made of sintered metal and the reaction mixture was passed continuously over the frit.

The conversion and the selectivity were determined by GC analysis (GC column: RTX® Amine, length=30 m, internal diameter=0.25 mm, film thickness=0.5 µm) and stated as area %. Table 10 shows the results obtained as a function of the reaction time.

TABLE 10

| Time [h] | TDA conversion [Area %] | MDACH selectivity [Area %] |
|---|---|---|
| 23 | 99.93 | 83.72 |
| 142 | 99.87 | 84.93 |
| 277 | 99.55 | 84.15 |

The example shows that the hydrogenation of TDA in a continuous suspension hydrogenation is possible without significant decline in the conversion and selectivity.

The invention claimed is:

1. A method comprising hydrogenating a mixture 2,4- and 2,6-diaminotoluene, in which the 2,4-diaminotoluene is present in a proportion of 70 to 90% by weight, and the 2,6-diaminotoluene is present in a proportion of 10 to 30% by weight, with hydrogen in the presence of a catalyst, wherein: the catalyst comprises ruthenium on a zirconium oxide support material;
   the zirconium oxide support material has a BET surface area of 50 to 100 m$^2$/g, a pore volume of 0.1 to 0.9 cm$^3$/g, and a tapped density of 700 to 1750 kg/m$^3$; and
   the catalyst has a BET surface area of 50 to 100 m$^2$/g, a pore volume of 0.1 to 0.9 cm$^3$/g, and a tapped density of 700 to 1750 kg/m$^3$.

2. The method according to claim 1, wherein the method is carried out continuously.

3. The method according to claim 1, wherein the method is carried out at a temperature of 50 to 220° C.

4. The method according to claim 1, wherein the method is carried out at a hydrogen pressure of 100 to 300 bar.

5. The method according to claim 1, wherein the catalyst comprises ruthenium in an amount of 0.05 to 20% by weight, based on a total weight of the catalyst.

6. The method according to claim 1, wherein the zirconium oxide support material is present in monoclinic, tetragonal, cubic or amorphous phase or a mixed phase of these modifications.

7. The method according to claim 1, wherein the zirconium oxide support material is present in monoclinic, tetragonal or a mixed phase of these modifications.

8. The method according to claim 1, wherein the zirconium oxide support material of the catalyst has a pore size distribution in which more than 50% of the pores present are formed by mesopores having a diameter of 2 nm to 50 nm and the remainder up to 100% by macropores having a diameter>50 nm.

9. The method according to claim 1, wherein the catalyst has a pore size distribution in which more than 50% of the pores present are formed by mesopores having a diameter of 2 nm to 50 nm and the remainder up to 100% by macropores having a diameter>50 nm.

10. The method according to claim 1, wherein the zirconium oxide support material of the catalyst has a pore size distribution in which more than 40% of the pores present are formed by macropores having a diameter of >50 nm and the remainder up to 100% by mesopores having a diameter of 2 nm to 50 nm.

11. The method according to claim 1, wherein the catalyst has a pore size distribution in which more than 40% of the pores present are formed by macropores having a diameter of >50 nm and the remainder up to 100% by mesopores having a diameter of 2 nm to 50 nm.

12. The method according to claim 1, wherein the hydrogenation is conducted in an organic solvent.

13. The method according to claim 1, wherein the catalyst is present in a fixed bed.

14. The method according to claim 1, wherein the catalyst is present in a suspension.

15. The method according to claim 1, wherein in the mixture of 2,4- and 2,6-diaminotoluene, the 2,4-diaminotoluene is present in a proportion of 75 to 85% by weight, and the 2,6-diaminotoluene is present in a proportion of 15 to 25% by weight.

* * * * *

UNITED STATES PATENT AND TRADEMARK OFFICE
CERTIFICATE OF CORRECTION

PATENT NO. : 10,329,237 B2
APPLICATION NO. : 15/103652
DATED : June 25, 2019
INVENTOR(S) : Bernd Bastian Schaack et al.

Page 1 of 1

It is certified that error appears in the above-identified patent and that said Letters Patent is hereby corrected as shown below:

In the Specification

In Column 9, Line 60, delete "MACH" and insert -- MDACH --

In the Claims

In Column 14, Line 39, Claim 1, after "mixture" insert -- of --

Signed and Sealed this
Nineteenth Day of May, 2020

Andrei Iancu
*Director of the United States Patent and Trademark Office*